US007792312B2

(12) United States Patent
Inoue et al.

(10) Patent No.: US 7,792,312 B2
(45) Date of Patent: Sep. 7, 2010

(54) ACTIVE NOISE CONTROL SYSTEM

(75) Inventors: Toshio Inoue, Tochigi-ken (JP); Akira Takahashi, Tochigi-ken (JP); Kosuke Sakamoto, Utsunomiya (JP); Yasunori Kobayashi, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 1065 days.

(21) Appl. No.: 11/500,418

(22) Filed: Aug. 8, 2006

(65) Prior Publication Data

US 2007/0038441 A1 Feb. 15, 2007

(30) Foreign Application Priority Data

Aug. 9, 2005 (JP) ............................ 2005-230552

(51) Int. Cl.
*H03B 29/00* (2006.01)
*G10K 11/16* (2006.01)
*A61F 11/06* (2006.01)

(52) U.S. Cl. ................. 381/71.9; 381/71.14; 381/71.4; 381/71.8; 381/86

(58) Field of Classification Search ..... 381/71.1–71.14, 381/80, 81, 86, 123, 94.1; 181/206
See application file for complete search history.

(56) References Cited

U.S. PATENT DOCUMENTS 4,506,380 A * 3/1985 Matsui ...................... 381/71.9
5,426,703 A * 6/1995 Hamabe et al. .......... 381/71.12
5,638,305 A * 6/1997 Kobayashi et al. .......... 700/280
5,701,349 A * 12/1997 Sano et al. ................. 381/71.4
5,910,993 A 6/1999 Aoki et al.
6,650,756 B1 * 11/2003 Saito et al. ............... 381/71.12
7,340,065 B2 * 3/2008 Nakamura et al. ....... 381/71.11
7,352,869 B2 * 4/2008 Inoue et al. .............. 381/71.11
7,574,006 B2 * 8/2009 Funayama et al. ....... 381/71.12
7,633,257 B2 * 12/2009 Sakamoto et al. ........... 318/611
2004/0240678 A1 12/2004 Nakamura et al.
2007/0140503 A1 * 6/2007 Sakamoto et al. .......... 381/71.4

FOREIGN PATENT DOCUMENTS

JP 06-250672 A 9/1994
JP 9-303477 A 11/1997
JP 3094517 B2 8/2000
JP 3198548 B2 6/2001
JP 2004-354657 A 12/2004

* cited by examiner

*Primary Examiner*—Xu Mei
(74) *Attorney, Agent, or Firm*—Arent Fox LLP

(57) ABSTRACT

An active noise control system prevents a continuous muffled sound from being generated as an abnormal sound under a high sound pressure from a speaker when a microphone as a sound detector is covered, and reduces noise immediately when the microphone is uncovered. A first threshold value as an upper limit value and a second threshold value as a lower limit value are provided for the filter coefficient of an adaptive notch filter. When the filter coefficient is greater than the first threshold value, a control sound is faded out according to a forgetting process. When the filter coefficient is smaller than the second threshold value, an adaptive control process is resumed. Even if the microphone is covered, the filter coefficient does not exceed the first threshold value as the upper limit value.

6 Claims, 8 Drawing Sheets

FORGETTING PROCESS (PERFORMED BY 2ND FILTER COEFFICIENT UPDATING MEANS)

ACTIVE NOISE CONTROL SYSTEM

BACKGROUND OF THE INVENTION

1. Field of the Invention

The present invention relates to an active noise control system for controlling noise with an adaptive notch filter, and more particularly to an active noise control system which is suitable for use in a closed space such as a compartment of a mobile object having a noise source such as an engine or the like. The mobile object may be a motor vehicle such as an automobile or the like, a ship, an amphibian, a pleasure boat, a helicopter, an airplane, or the like.

2. Description of the Related Art

There have recently been proposed active noise control systems for controlling noise such as engine sounds, road noise, etc. heard in the passenger compartment of motor vehicles with control sounds radiated from speakers for reducing the noise at the ears of passengers in the passenger compartment.

It has been pointed out that when such active noise control systems fail to have an initial performance capability due to aging, the performance capability failure tends to disperse the control sound, which may possibly be output as an abnormal sound under high sound pressure from the speaker (see Japanese Patent No. 3198548 and Japanese Patent No. 3094517).

The inventors of the present application have found that even if an active noise control system operates normally (without aging), it may produce an abnormal sound under high sound pressure. Specifically, a microphone for detecting a canceling error sound representing the difference between the noise and the control sound and outputting an error signal has a sound input region, specifically, an opening defined, e.g., in a lining in the compartment of the mobile object with the microphone fixed in the lining, which may be accidentally or intentionally closed by the palm of a hand of a passenger or the like, resulting in a microphone opening closed state. When the microphone opening is closed, the gain of transfer characteristics from the speaker to the microphone is reduced, and, as a result, the control signal supplied from the adaptive notch filter to the speaker increases in level. Therefore, the control sound that is output from the speaker depending on the control signal has an unnecessarily large sound pressure, producing an abnormal sound (continuous muffled sound). The continuous muffled sound may be imagined as seashell sound that one can hear when both ears are cupped by hands or large seashells.

If the technologies of Japanese Patent No. 3198548 and Japanese Patent No. 3094517 are applied to prevent the continuous muffled sound from being produced, then control details need to be changed, e.g., updating quantities for the filter coefficients of the adaptive notch filters need to be changed or transfer functions need to be changed or convergent coefficients need to be reduced when a dispersion of the control sound is detected from the values of the filter coefficients, or the control process needs to be shut down. Therefore, when the passenger removes its hand off the microphone opening, canceling the microphone opening closed state, it is impossible to immediately perform the adaptive control process for reducing noise.

SUMMARY OF THE INVENTION

It is an object of the present invention to provide an active noise control system which is capable of preventing a continuous muffled sound from being produced when a sound detector such as a microphone or the like is closed and which is capable of immediately reducing noise according to an active control process when the sound detector is released from a closed state.

According to the present invention, there is provided an active noise control system comprising: a base signal generator for outputting a harmonic base signal from the frequency of noise generated by a noise source; an adaptive notch filter for being supplied with the base signal and outputting a control signal for canceling out the noise; a sound output unit for outputting a control sound represented by the control signal; a sound detector for detecting a canceling error sound representing the difference between the noise and the control sound and outputting an error signal; a correcting filter having a transfer function from the sound output unit to the sound detector, for being supplied with the base signal and outputting a reference signal; first filter coefficient updating means for being supplied with the error signal and the reference signal and successively updating a filter coefficient of the adaptive notch filter in order to minimize the error signal; second filter coefficient updating means for updating the filter coefficient by multiplying the filter coefficient to be updated of the adaptive notch filter by a predetermined value smaller than 1; and switching means for alternatively switching between the first filter coefficient updating means and the second filter coefficient updating means and supplying the filter coefficient to the adaptive notch filter; wherein the switching means switches to a filter coefficient supplied from the second filter coefficient updating means when the filter coefficient is equal to or greater than a first threshold value and switches to a filter coefficient supplied from the first filter coefficient updating means when the filter coefficient is smaller than a second threshold value which is smaller than the first threshold value.

According to the present invention, in order to prevent a continuous muffled sound from being generated when the sound detector such as a microphone is covered, when the filter coefficient (first filter coefficient) of the adaptive notch filter is greater than the first threshold value, a forgetting process is performed to generate a canceling sound using a corrected filter coefficient (second filter coefficient) which is produced by successively multiplying the filter coefficient to be updated (the first filter coefficient) by a predetermined value smaller than 1, e.g., a value of $127/128 \approx 0.99$. If the filter coefficient (the second filter coefficient) is of a value smaller than the second threshold value which is smaller than the first threshold value while the canceling sound is being generated, then an adaptive control process is resumed, and the canceling sound is generated using the coefficient (the first filter coefficient) that is successively updated to minimize the error sound.

As described above, the upper limit value (the first threshold value) and the lower limit value (the second threshold value) are provided for the filter coefficient. When the filter coefficient is greater than the upper limit value, a control sound is faded out according to a forgetting process. When the filter coefficient is smaller than the lower limit value, the adaptive control process is resumed. Even if the sound detector is covered, the filter coefficient does not exceed the upper limit value, preventing a continuous muffled sound from being generated. Since a noise cancellation process is continued, noise can immediately be lowered when the sound detector is uncovered.

If the forgetting process for fading out the control sound is not performed, but the control sound is abruptly stopped, then a sudden muffled sound is generated. For preventing such a sudden muffled sound from being generated and returning from the forgetting process immediately to the adaptive control process, the control sound may be converged to a value small enough for passengers not to sense the control sound within about 0.1 second. It has experimentally been found that the predetermined value smaller than 1 should preferably be a value greater than 0.9 (0.9<predetermined value<1.0).

The base signal generator outputs a base sine wave signal and a base cosine wave signal as the harmonic base signal. The adaptive notch filter comprises a first adaptive notch filter for outputting a first control signal based on the base cosine wave signal, a second adaptive notch filter for outputting a second control signal based on the base sine wave signal, and an adder for adding the first control signal and the second control signal into the control signal and outputting the control signal to the sound output unit. The switching means switches to a filter coefficient supplied from the second filter coefficient updating means for the first adaptive notch filter and the second adaptive notch filter when either one of filter coefficients supplied respectively to the first adaptive notch filter and the second adaptive notch filter is equal to or greater than the first threshold value, and switches to a filter coefficient supplied from the first filter coefficient updating means for the first adaptive notch filter and the second adaptive notch filter when either one of the filter coefficients supplied respectively to the first adaptive notch filter and the second adaptive notch filter is smaller than the second threshold value which is smaller than the first threshold value, thereby achieving certain effects.

The first threshold value and the second threshold value may vary depending on the frequency of the base signal. The sound pressure of noise which makes passengers feel uncomfortable differs depending on the frequency thereof. With the first and second threshold values being variable, since the control sound is faded out dependent on the frequency of the base signal, i.e., the frequency of the noise (continuous muffled sound) to be reduced, the uncomfortable continuous muffled sound is more appropriately prevented from being generated.

According to the present invention, the continuous muffled sound is prevented from being generated when the sound detector is covered, and the noise is reduced immediately when the sound detector is uncovered.

The above and other objects and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Preferred embodiments of the present invention will be described below with reference to the drawings.

Figure 1:
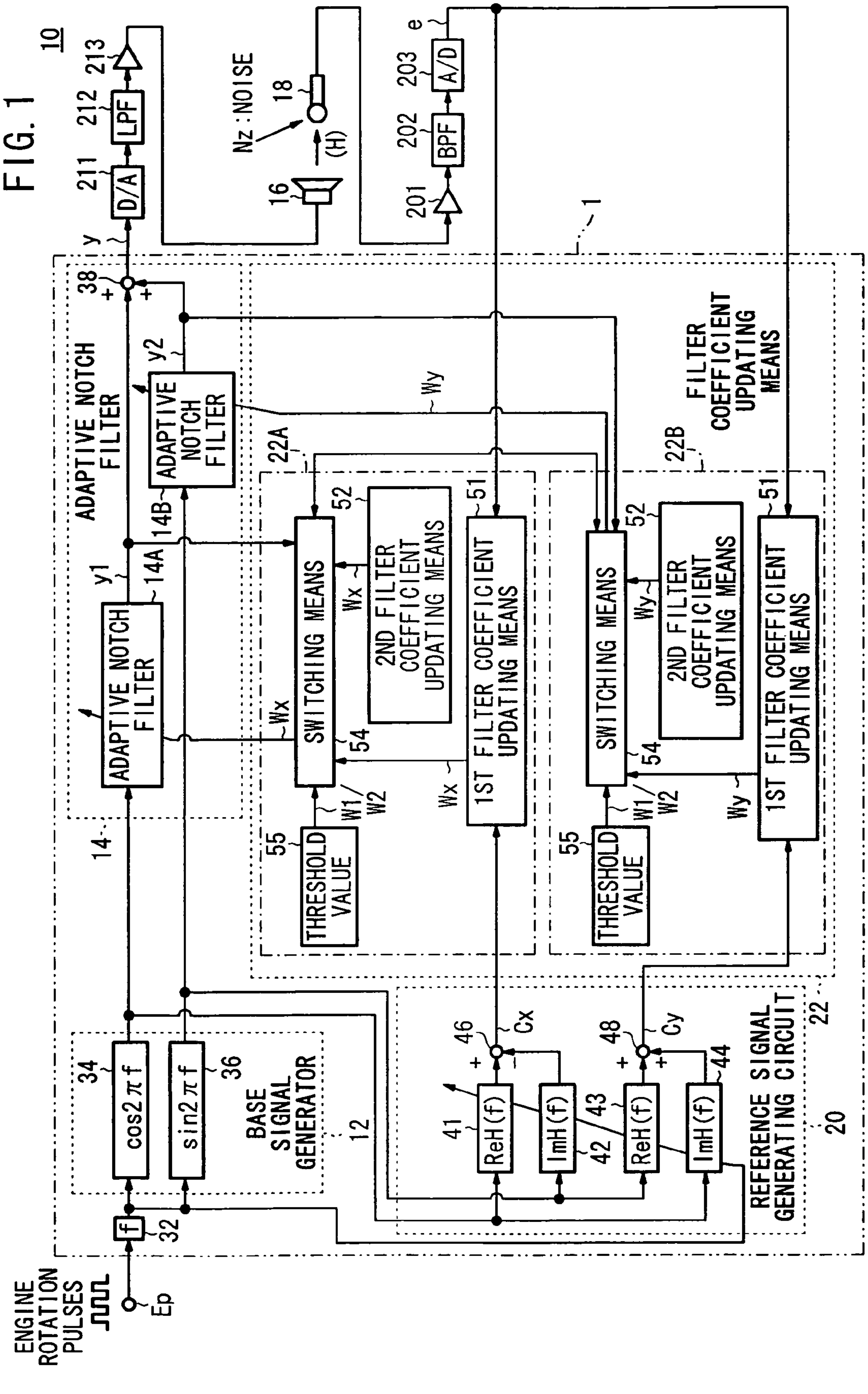
FIG. 1 is a block diagram of an active noise control system according to an embodiment of the present invention.

FIG. 1 shows in block form an active noise control system 10 according to an embodiment of the present invention. The active noise control system 10 is basically implemented by a microcomputer (control means) 1.

Figure 2:
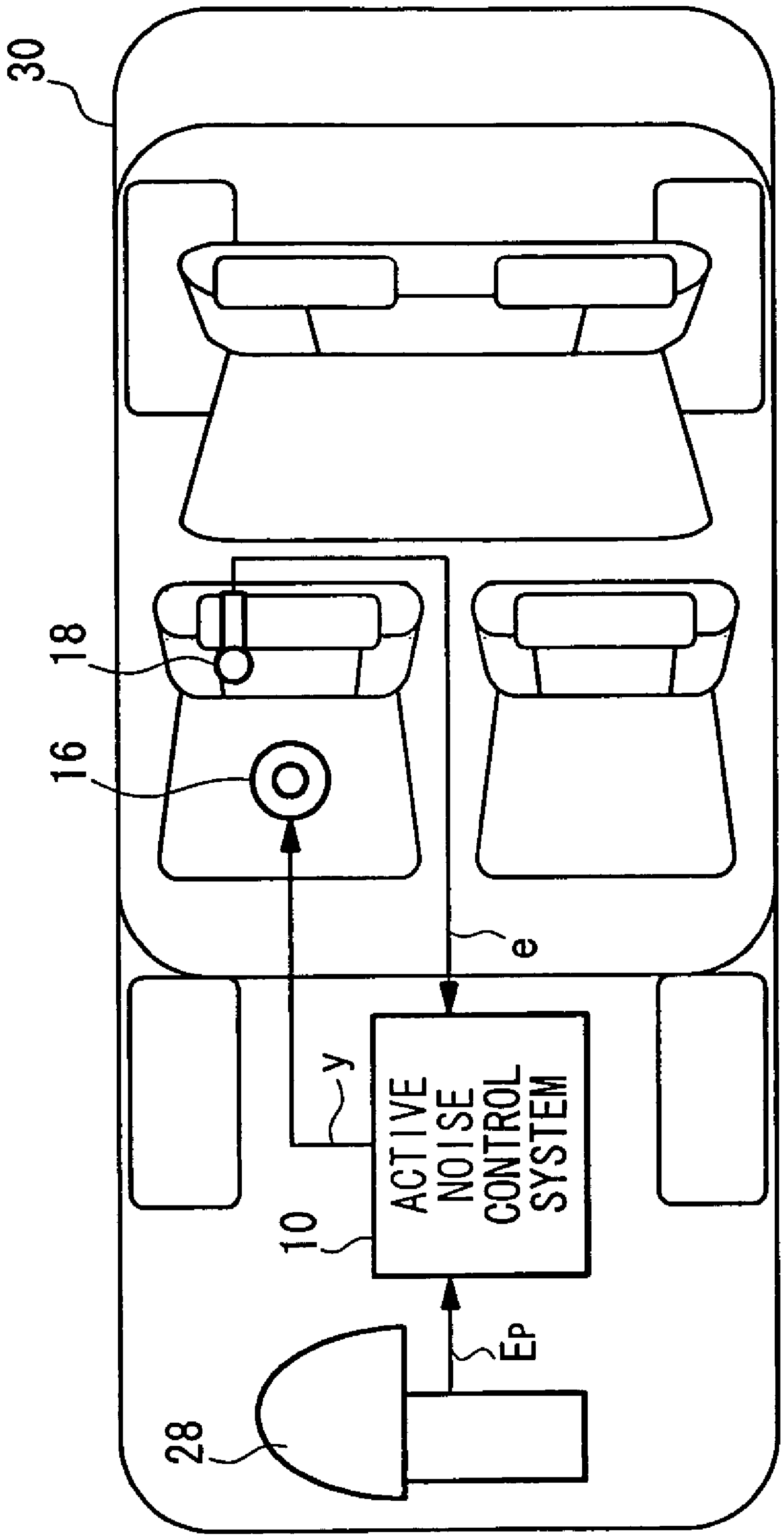
FIG. 2 is a schematic plan view of a motor vehicle incorporating the active noise control system therein.

FIG. 2 schematically shows a motor vehicle 30 which is a mobile object having an engine 28, the motor vehicle 30 incorporating the active noise control system 10 (shown in FIG. 1) therein.

As shown in FIG. 1, the active noise control system 10 basically comprises a base signal generator 12 for generating a harmonic base signal from the frequency f of noise Nz that is generated by an engine 28 as a noise source, an adaptive notch filter 14 for being supplied with the base signal as its input and outputting a control signal y(n) to cancel out the noise Nz at time n in each sampling period, a speaker 16 as a sound output unit for outputting a control sound represented by a control signal y(n), a microphone 18 as a sound detector for detecting a canceling error sound representing the difference between the noise Nz from the engine 28 and the control sound from the speaker 16 and outputting an error signal e(n), a reference signal generating circuit 20 having a transfer function H of a sound field from the position of the speaker 16 to the position of the microphone 18, for outputting a reference signal in response to the base signal applied thereto, and a filter coefficient updating means (LMS algorithm processor) 22 for being supplied with the error signal e(n) and the reference signal to update filter coefficients W(n+1) of the adaptive notch filter 14.

The filter coefficient updating means 22 comprises filter coefficient updating means 22A and filter coefficient updating means 22B.

As schematically shown in FIG. 2, the active noise control system 10 is disposed below the dashboard of the motor vehicle 30. The active noise control system 10 is supplied with engine rotation pulses Ep from a rotation sensor for detecting the rotation of a main shaft of the engine 28 which is mounted on the chassis of the motor vehicle 30 below the engine hood, and an error signal e(n) from the microphone 18 which is fixed to a roof lining over the driver's seat of the motor vehicle 30. The active noise control system 10 outputs a control signal y(n) to the speaker 16 which is disposed below the driver's seat for producing a control sound in response to the control signal y(n). In the present embodiment, the active noise control system 10 will be described for performing active noise control for the driver's seat only. However, the principles of the active noise control system 10 are equally applicable to perform active noise control for other seats, e.g., a front passenger's seat or rear passenger's seats.

Figure 3:
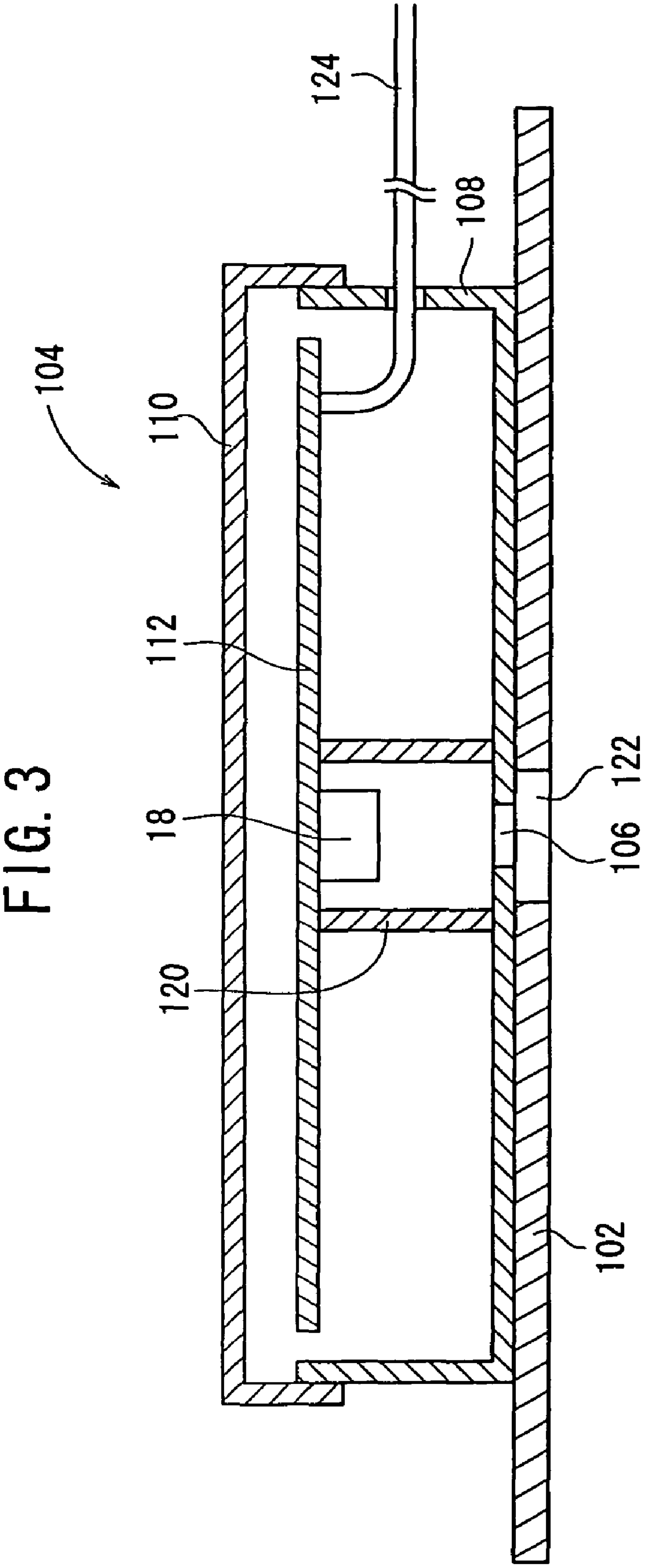
FIG. 3 is a cross-sectional view of a microphone unit fixedly mounted on a roof lining of the motor vehicle.

FIG. 3 shows in cross section a microphone unit 104 fixedly mounted on the roof lining, denoted by 102, of the motor vehicle 30.

As shown in FIG. 3, the microphone unit 104 comprises a lower casing 108 disposed on the roof lining 102 and having a central opening 106 defined therein, and an upper casing 110 mounted on the lower casing 108. The microphone 18 is housed in a space defined between the lower casing 108 and the upper casing 110 and shielded against the entry of external sounds. The microphone 18 is mounted on a surface of the printed-wiring board 112 which is connected to a surface of the lower casing 108 around the opening 106 by a tubular structural body 120 which provides a shielded sound passage extending from the opening 106 to the microphone 18.

The roof lining 102 has an opening 122 defined therein coaxially with the opening 106. The opening 122 is greater in diameter than the opening 106 and held in direct communication with the opening 106. Therefore, the opening 122, the opening 106, and the shielded sound passage provided by the tubular structural body 120 in the microphone unit 104 jointly serve to guide only sounds (noise and control sound for canceling the noise) in the passenger compartment to be applied to the microphone 18. The microphone unit 104 has an output cable 124 connected to the microphone 18 and extending out of the lower casing 108. The output cable 124 outputs from the microphone unit 104 an error signal e(n) relative to the noise and the control sound through an amplifier 201, a BPF (BandPass Filter) 202, and an A/D converter 203, which are mounted on the printed-wiring board 112. The error signal e(n) is converted into a digital signal by the A/D converter 203.

When the opening 122 in the roof lining 102 is closed by the palm of a hand of a passenger or the like, the opening 106 is essentially closed. At this time, the conventional active noise control system would cause the speaker 16 to output a control sound under a high sound pressure as an abnormal sound (continuous muffled sound).

According to the present embodiment, the active noise control system 10 shown in FIGS. 1 and 2 controls the control sound to be produced under a predetermined sound pressure so that the passengers will not hear the control sound as an uncomfortable continuous muffled sound.

As shown in FIG. 1, a frequency counter 32 detects the frequency f of noise Nz from the engine rotation pulses Ep, and supplies the detected frequency f to the base signal generator 12 and the reference signal generating circuit 20.

The base signal generator 12 comprises a cosine wave generator 34 for generating a base wave signal representing a cosine wave cos {2π(f, n)} that is a harmonic base signal from the frequency f of the noise Nz and a sine wave generator 36 for generating a base wave signal representing a sine wave sin {2π(f, n)} that is a harmonic base signal from the frequency f of the noise Nz.

The adaptive notch filter 14 comprises an adaptive notch filter (first adaptive notch filter) 14A which is supplied with the cosine wave cos {2π(f, n)} and an adaptive notch filter (second adaptive notch filter) 14B which is supplied with the sine wave sin {2π(f, n)}. The adaptive notch filter 14A, when supplied with the cosine wave cos {2π(f, n)}, outputs a control signal (first control signal) y1(*n*), and the adaptive notch filter 14B, when supplied with the sine wave sin {2π(f, n)}, outputs a control signal (second control signal) y2(*n*). The control signals y1(*n*), y2(*n*) are added by an adder 38 into a control signal y(n) which is a digital signal having a given phase and amplitude. The digital control signal y(n) is converted by a D/A converter 211 into an analog control signal, which is supplied through a LPF (Low-Pass Filter) 212 and an amplifier 213 to a speaker 16. Based on the supplied control signal, the speaker 16 outputs a control sound.

The reference signal generating circuit 20 comprises four correcting filters 41, 42, 43, 44 and two adders 46, 48.

The correcting filters 41, 43 have characteristics ReH(f) representing the real part of the transfer function H of a sound field from the position of the speaker 16 to the position of the microphone 18. The correcting filters 42, 44 have characteristics ImH(f) representing the imaginary part of the same transfer function H.

The transfer function H as claimed and described thus far is a transfer function for signals from the position of the speaker 16 to the position of the microphone 18 in the passenger compartment. An actual transfer function is measured as follows: A signal transfer characteristics measuring apparatus such as a Fourier transformation apparatus, for example, is connected between the input of the D/A converter 211 (the output of the adder 38) and the output of the A/D converter 203 (the input of the filter coefficient updating means 22). The signal transfer characteristics measuring apparatus measures the transfer function of a signal based on the control signal y(n) that is output from the microcomputer 1 to the input of the D/A converter 211 and the error signal e(n) that is input from the microphone 18 through the A/D converter 203 to the microcomputer 1.

Therefore, on account of the process of measuring the signal transfer function, the transfer function for signals between the speaker 16 and the microphone 18 in the passenger compartment also include transfer characteristics due to analog electronic circuits inserted between the output and input of the microcomputer 1, e.g., the speaker 16, the microphone 18, the D/A converter 211, the LPF 212, the amplifier 213, the amplifier 201, the BPF 202, and the A/D converter 203.

Stated otherwise, depending on the process of measuring the signal transfer function, the transfer function H for signals between the speaker 16 and the microphone 18 in the passenger compartment represents transfer function characteristics from the output of the adaptive notch filter 14 to the input of the filter coefficient updating means 22.

The real-part characteristics ReH(f) and the imaginary-part characteristics ImH(f) have their characteristic values variable depending on the frequency f.

The adder 46 outputs a reference signal (corrective value) Cx(n) relative to the cosine wave cos {2π(f, n)} to the filter coefficient updating means 22A, and the adder 48 outputs a reference signal (corrective value) Cy(n) relative to the sine wave sin {2π(f, n)} to the filter coefficient updating means 22B.

As can be understood from the circuit connections of the reference signal generating circuit 20, the reference signals Cx(n), Cy(n) are calculated according to the following equations:

$$Cx(n)=\cos\{2\pi(f,n)\}\cdot ReH(f)-\sin\{2\pi(f,n)\}\cdot ImH(f)$$

$$Cy(n)=\cos\{2\pi(f,n)\}\cdot ImH(f)+\sin\{2\pi(f,n)\}\cdot ReH(f)$$

If both reference signals Cx(n), Cy(n) or only either one of them is to be referred to, then they are represented by C(n).

The filter coefficient updating means 22A sets an updated filter coefficient Wx(n+1) as a new filter coefficient W(n)=Wx(n) in the adaptive notch filter 14A through a switching means 54 (n←n+1). The filter coefficient updating means 22B sets an updated filter coefficient Wy(n+1) as a new filter coefficient W(n)=Wy(n) in the adaptive notch filter 14B through a switching means 54 (n←n+1).

The filter coefficient updating means 22A, 22B comprise: respective first filter coefficient updating means 51 for being supplied with the error signal e(n) and the reference signals Cx(n), Cy(n), respectively, and successively updating the filter coefficient W(n) [W(n+1)=W(n)+ΔW {ΔW=−μe(n)c(n) represents an updating quantity that is calculated by an adaptive algorithm (LMS algorithm) so as to minimize the square of the error signal e(n) based on the reference signal c(n) and the error signal e(n), where μ represents a constant}] at respective times n so as to minimize the error signal e(n); respective second coefficient updating means 52 for updating the filter coefficient {W(n+1)=W(n)×λ} by multiplying the filter coefficient W(n) to be updated by a predetermined value λ smaller than 1 (e.g., λ=127/128≈0.99); and respective switching means 54 for alternatively selecting one of the updated filter coefficients W(n+1), i.e., W(n+1)=W(n)+ΔW or W(n+1)=W(n)×λ, supplied thereto.

In each of the filter coefficient updating means 22A, 22B, a threshold value setting means 55 is connected to the switching means 54. The threshold value setting means 55 sets a first threshold value (upper limit threshold value) W1 and a second threshold value (lower limit threshold value) W2 for the switching means 54. The first threshold value W1 and the second threshold value W2 are determined in advance by tests on actual motor vehicles and simulations or the like. The first threshold value W1 as the upper limit threshold value is set to a value which will not be exceeded while the active noise control system is operating normally, and the second threshold value W2 as the lower limit threshold value is set to a value which corresponds to a sound level that will not be sensed by the passengers while the motor vehicle is in motion.

The first threshold value W1 and the second threshold value W2 may be made variable depending on the frequency of the engine rotation pulses Ep, or in other words, the frequency f of the base signal. If the first threshold value W1 and the second threshold value W2 are thus variable, then the threshold value setting means 55 is supplied with the frequency f from the frequency counter 32, and maps of the threshold values W1, W2 depending on the frequency f are stored in the threshold value setting means 55.

For example, when the engine rotational speed is in a relatively high range and the generated noise is of a relatively high level, the first threshold value W1 (referred to as W1loud) and the second threshold value W2 (referred to as W2loud) may be set to respective values which are greater than the first threshold value W1 (referred to as W1small) and the second threshold value W2 (referred to as W2small) when the engine rotational speed is in a relatively low range and the generated noise is of a relatively low level. For example, these threshold values may be set according to the relationship: W1loud>W1small>W2loud>W2small.

The first filter coefficient updating means 51 calculates the filter coefficient W(n+1)=W(n)+ΔW according to an ordinary adaptive control process, and the second filter coefficient updating means 52 calculates the filter coefficient W(n+1)=W(n)×λ according to a forgetting process.

If the filter coefficient W(n) supplied from the first filter coefficient updating means 51 to the adaptive notch filter 14A (14B) is equal to or greater than the first threshold value W1 successively a predetermined number of times, then the switching means 54 makes a switching action to supply the adaptive notch filter 14A (14B) with the updated filter coefficient W(n+1)=W(n)×λ that is supplied from the second filter coefficient updating means 52. Thereafter, if the filter coefficient W(n) supplied from the second filter coefficient updating means 52 becomes smaller than the second threshold value W2, then the switching means 54 makes a switching action to supply the adaptive notch filter 14A (14B) with the updated filter coefficient W(n+1)=W(n)+ΔW that is supplied from the first filter coefficient updating means 51.

The switching means 54 of the filter coefficient updating means 22A, 22B are connected to each other. These switching means 54 are operated correlatively such that when either one of the switching means 54 switches from the filter coefficient W(n+1)=W(n)+ΔW to the filter coefficient W(n+1)=W(n)×λ and outputs the filter coefficient W(n+1)=W(n)×λ, the other switching means 54 also switches from the filter coefficient W(n+1)=W(n)+ΔW to the filter coefficient W(n+1)=W(n)×λ and outputs the filter coefficient W(n+1)=W(n)×λ, and when either one of the switching means 54 switches from the filter coefficient W(n+1)=W(n)×λ to the filter coefficient W(n+1)=W(n)+ΔW and outputs the filter coefficient W(n+1)=W(n)+ΔW, the other switching means 54 also switches from the filter coefficient W(n+1)=W(n)×λ to the filter coefficient W(n+1)=W(n)+ΔW and outputs the filter coefficient W(n+1)=W(n)+ΔW. In other words, the adaptive notch filter 14A for outputting the control signal y1(*n*) and the filter coefficient updating means 22A, and the adaptive notch filter 14B for outputting the control signal y2(*n*) and the filter coefficient updating means 22B operate to perform the ordinary adaptive control process substantially simultaneously and also to perform the forgetting process simultaneously.

The active noise control system 10 is basically constructed and operates as described above. Details of operation of the active noise control system 10 will be described below with reference to flowcharts shown in FIGS. 4 through 6 which are representative of a program executed by the microcomputer 1.

As described above, the adaptive notch filter 14A for outputting the control signal y1(*n*) and the filter coefficient updating means 22A, and the adaptive notch filter 14B for outputting the control signal y2(*n*) and the filter coefficient updating means 22B operate to perform the ordinary adaptive control process substantially simultaneously and also to perform the forgetting process simultaneously. Therefore, for the sake of brevity, only operation of the adaptive notch filter 14A for outputting the control signal y1(*n*) and the filter coefficient updating means 22A will be described below.

Figure 4:
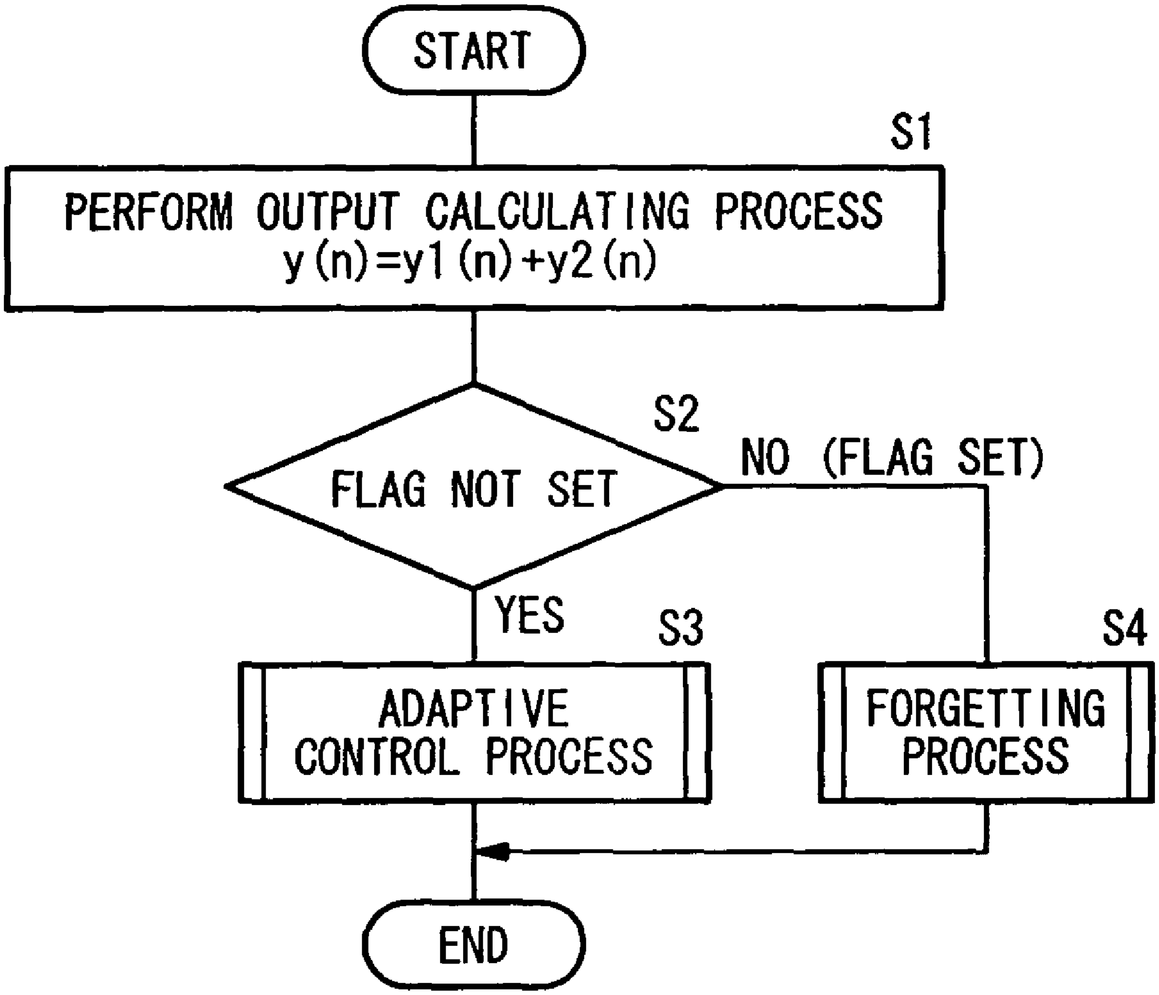
FIG. 4 is a flowchart of an operation sequence of the active noise control system.
Figure 5:
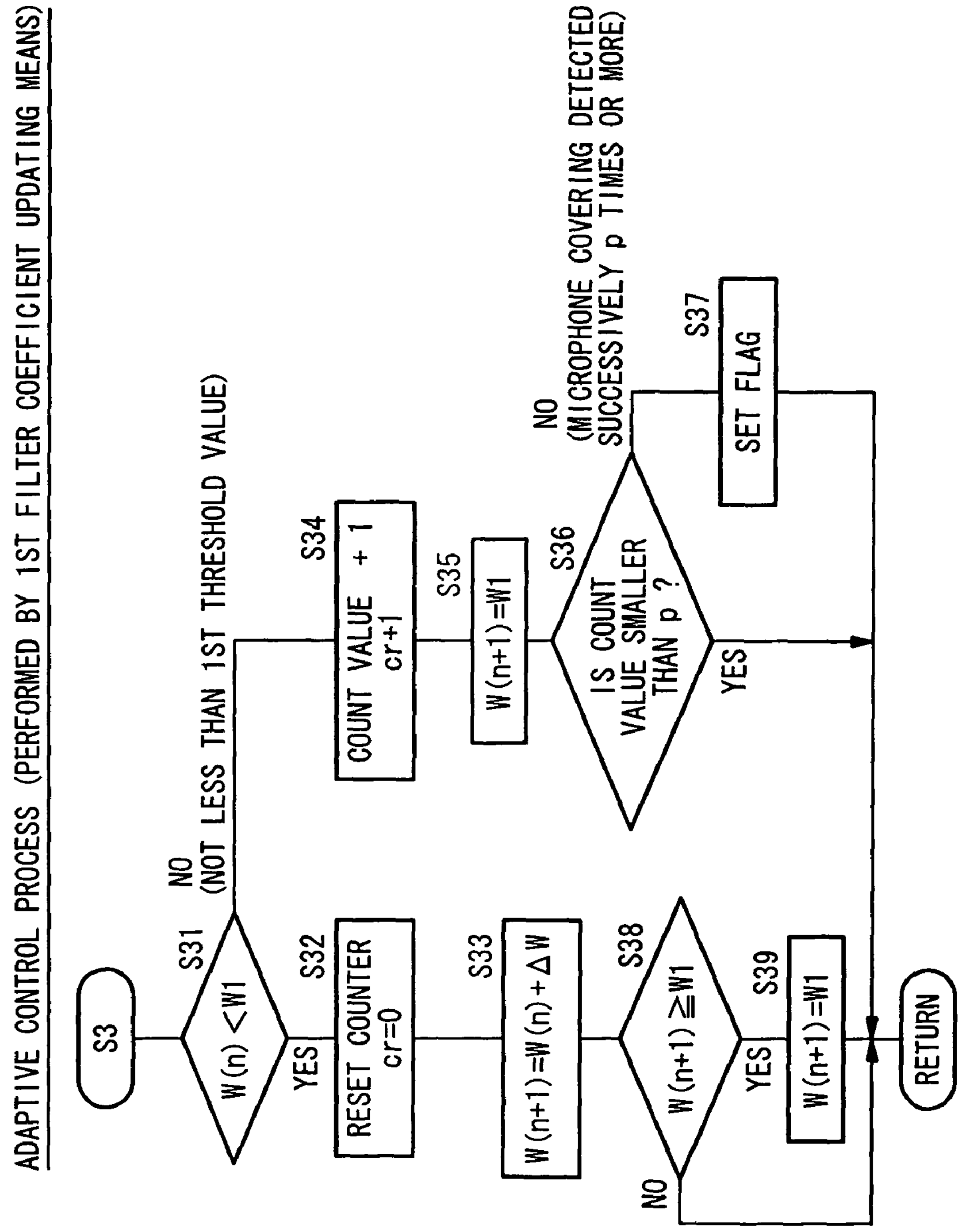
FIG. 5 is a flowchart of an operation sequence of an adaptive control process including a process for limiting an upper limit value for a filter coefficient.
Figure 6:
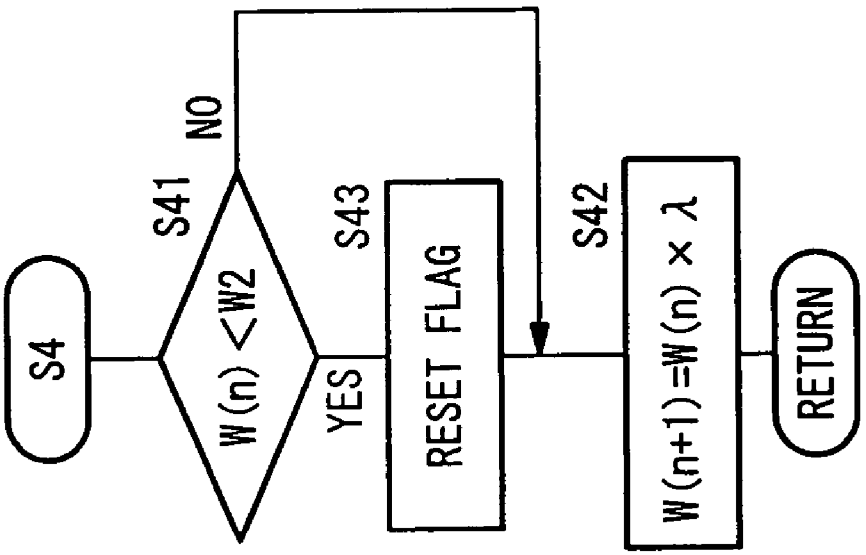
FIG. 6 is a flowchart of an operation sequence of a forgetting process including a process for limiting a lower limit value for a filter coefficient.
Figure 7A:
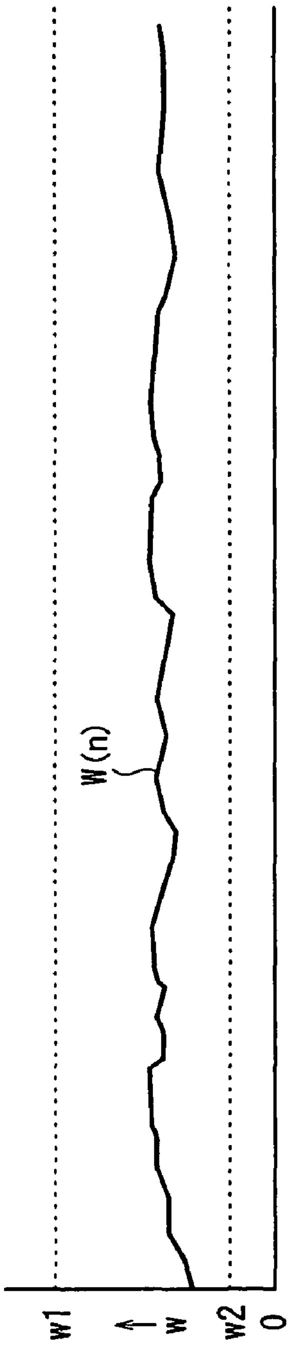
FIG. 7A is a timing chart showing how a filter coefficient changes in an ordinary operating state.
Figure 7B:
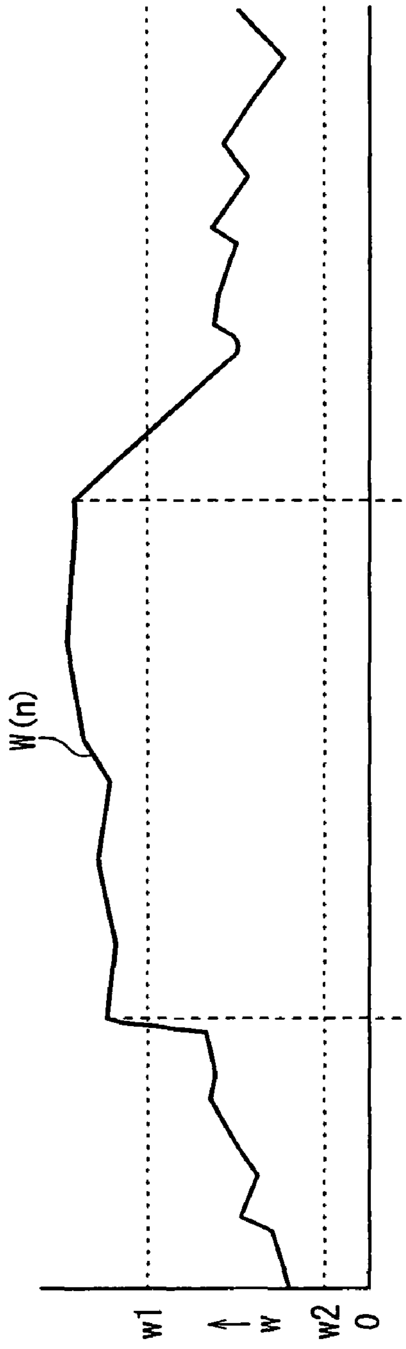
FIG. 7B is a timing chart showing how a filter coefficient changes when an abnormal sound is generated.
Figure 7C:
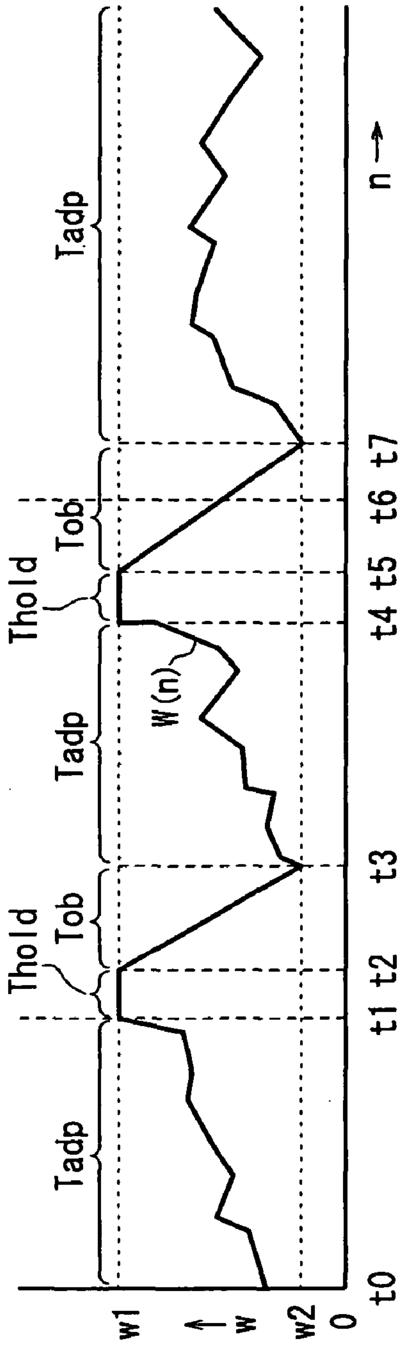
FIG. 7C is a timing chart showing how a filter coefficient of the active noise control system according to the embodiment changes.

Timing charts shown in FIGS. 7A, 7B, 7C will also be referred to in addition to the flowcharts shown in FIGS. 4 through 6. The timing chart shown in FIG. 7A illustrates the ordinary adaptive control process when the microphone opening is not closed and the filter coefficient W(n) is of a value between the first threshold value W1 and the second threshold value W2. The timing chart shown in FIG. 7B illustrates the manner in which a continuous muffled sound is generated by the conventional active noise control system which performs only the ordinary adaptive control process. The timing chart shown in FIG. 7C illustrates the manner in which the active noise control system 10 according to the present embodiment operates to prevent a continuous muffled sound from being generated even when the opening 106 of the microphone unit 104 is closed and also to return to the ordinary adaptive control process immediately when the closure of the opening of the microphone unit 104 is canceled, i.e., when the opening of the microphone unit 104 is uncovered.

In FIG. 7C, each of a period from time t0 to time t1, a period from time t3 to time t4, and a period from time t7 represents an adaptive control process time Tadp. Each of a period from time t1 to time t2 and a period from time t4 to time t5 represents a period Thold for holding the second threshold value W1 which serves as the upper limit value for the filter coefficient W(n). Each of a period from time t2 to time t3 and a period from time t4 to time t5 represents a forgetting process time Tob.

In FIG. 7B, a period from time t1 to time t6 represents a period in which a muffling sound as an abnormal sound under a high sound pressure is generated.

In step S1 shown in FIG. 4, an output calculating process is performed at time n. Specifically, the frequency counter 32 detects a frequency f from engine rotation pulses Ep and supplies the detected frequency f to the base signal generator 12 and the reference signal generating circuit 20.

The cosine wave generator 34 of the base signal generator 12 generates a base wave signal representing a cosine wave cos {2π(f, n)} from the detected frequency f and supplies the generated base wave signal to the adaptive notch filter 14A and the correcting filters 41, 44 of the reference signal generating circuit 20. The sine wave generator 36 of the base signal generator 12 generates a base wave signal representing a sine wave sin {2π(f, n)} from the frequency f and supplies the generated base wave signal to the adaptive notch filter 14B and the correcting filters 42, 43 of the reference signal generating circuit 20.

The adaptive notch filters 14A, 14B multiply the respective base signals cos {2π(f, n)}, sin {2π(f, n)} by respective filter coefficients Wx(n), Wy(n), and output respective control signals y1(*n*), y2(*n*) to the adder 38.

The adder 38 adds the control signals y1(*n*), y2(*n*) into a control signal y(n) {y(n)=y1(*n*)+y2(*n*)}. The control signals y1(*n*), y2(*n*) are expressed as follows:

$$y1(n)=\cos\{2\pi(f,n)\}\cdot Wx(n)$$

$$y2(n)=\sin\{2\pi(f,n)\}\cdot Wy(n)$$

The correcting filters 41, 42 have their gains adjusted by the frequency f and supply respective output signals to the adder 46, which outputs a reference signal Cx(n) relative to the cosine wave cos {2π(f, n)} to the filter coefficient updating means 22A. The correcting filters 43, 44 have their gains adjusted by the frequency f and supply respective output signals to the adder 48, which outputs a reference signal Cy(n) relative to the sine wave sin {2π(f, n)} to the filter coefficient updating means 22B.

In step S2, it is determined whether a microphone opening closure flag (opening closure flag) Fm is set or not. If the microphone opening closure flag Fm is not set, then it is judged that the opening 106 of the microphone unit 104 is not closed (not in the microphone opening closed state). The first filter coefficient updating means 51 are selected, and an adaptive control process in step S3 is performed. The adaptive control process in step S3 are shown in detail in FIG. 5.

According to the adaptive control process, it is determined whether W(n) is smaller than the first threshold value W1 (see FIG. 7C) or not in step S31 shown in FIG. 5. If W(n) is smaller than the first threshold value W1 {W(n)<W1}, then it is judged that the adaptive noise control system in an ordinary operating state with no muffling sound generated. In step S32, the count value cr of a counter for determining the generation of a continuous muffled sound with a count value (continuous muffled sound determining value) p (e.g., p=10) is reset to zero (cr=0).

In step S33, the first filter coefficient updating means 51 perform the ordinary adaptive control process. Specifically, the first filter coefficient updating means 51 of the filter coefficient updating means 22A, 22B update the filter coefficient W(n) into a filter coefficient W(n+1)=W(n)+ΔW, as described above.

Then, in step S38, it is determined whether or not the filter coefficient W(n+1) calculated in step S33 is equal to or greater than the first threshold value W1. If W(n+1)=W1, then the filter coefficient W(n+1) is set to the first threshold value W1 {W(n+1)=W1}. Therefore, the control signal y(n) is kept as a preset upper limit value corresponding to the filter coefficient W1, preventing an uncomfortable muffling sound from being generated.

If the filter coefficient W(n) is equal to or greater than the first threshold value W1 {W(n)≧W1} in step S31, then it is judged that the opening 106 of the microphone unit 104 is closed. The count value cr is incremented by 1 (cr=cr+1) in step S34. In step S35, the first filter coefficient updating means 51 sets the first threshold value W1 as the filter coefficient W(n+1) so that the filter coefficient W(n) will not be of a greater value {W(n+1)=W1}.

In step S36, it is determined whether the count value cr is smaller than a determining value p for starting the forgetting process (a determining value p for the microphone opening closed state) or not. If the count value cr is smaller than the determining value p for the microphone opening closed state (cr<p), then control goes back to step S1. At this time, since the first filter coefficient updating means 51 sets the filter coefficient W(n)=W1 for the adaptive notch filter 14, the control signal y(n) is kept as the preset upper limit value corresponding to the filter coefficient W1, preventing an uncomfortable muffling sound from being generated (the period from time t1 to time t2 or the period from time t4 to time t5 in FIG. 7C).

According to the conventional adaptive control process, as shown in FIG. 7B, a muffling sound as an abnormal sound under a high sound pressure is generated after time t1 and continues to be generated until time t6 when the microphone opening closed state is canceled.

According to the active noise control system 10, however, as shown in FIG. 7C, a muffling sound is prevented from being generated in all periods from t1 to time t6.

If the count value Cr is equal to or greater than the determining value p for starting the forgetting process (cr≧p), then the microphone opening closure flag Fm is set in step S37. Specifically, if the microphone opening closed state detected in step S31 occurs as judged negatively in step S35 successively p times, then the microphone opening closure flag Fm is set, determining the microphone opening closed state (corresponding to times t2, t5 in FIG. 7C). Since step S35 has been carried out at times t2, t5, the filter coefficient W(n)=W1 is set for the adaptive notch filter 14 in the period from t1 to t2 and the period from t4 to time t5. Therefore, the control signal y(n) is kept as the preset upper limit value, preventing an uncomfortable muffling sound from being generated.

After the microphone opening closed state has been determined, since the microphone opening closure flag Fm is detected as being set in step S2 in a next cycle, the entity for executing the program changes from the first filter coefficient updating means 51 to the second filter coefficient updating means 52 for performing the forgetting process in step S4.

FIG. 6 shows in detail an operation sequence of the forgetting process.

In step S41 shown in FIG. 6, it is determined whether the filter coefficient W(n) is smaller than the second threshold value W2 or not. If the filter coefficient W(n) is not smaller than the second threshold value W2, i.e., if it is judged that the filter coefficient W(n) is of a value between the first threshold value W1 and the second threshold value W2 {W1>W(n) ≧W2}, the second filter coefficient updating means 52 performs a process of updating the filter coefficient W(n) into the filter coefficient W(n+1)=W(n)×λ in step S42.

Specifically, in step S42, the second filter coefficient updating means 52 sets the filter coefficient W(n+1)=W(n)×λ, which is produced by multiplying the filter coefficient W(n) to be updated by a predetermined value of 1 or smaller, as the filter coefficient W(n+1) in the adaptive notch filter 14. The forgetting process in which the filter coefficient W(n) is reduced and the control signal y(n) is reduced is now started (corresponding to times t2, t5 in FIG. 7C).

If the forgetting process for fading out the control sound is not performed, but the control signal y(n) is abruptly converged to “0”, then a sudden muffled sound is generated by the speaker 16. For preventing such a sudden muffled sound from being generated and returning from the forgetting process immediately to the adaptive control process, the control signal y(n) may be converged to a value small enough for the passengers not to sense the control sound within about 0.1 second. It has experimentally been found that the predetermined value λ smaller than 1 should preferably be a value greater than 0.9 ($0.9<\lambda<1.0$).

When the forgetting process from step S1 to step S2 (NO) to step S41 (NO) to step S42 is repeated a predetermined number of times (corresponding to the period from t2 to time t3 and the period from time t5 to time t7 in FIG. 7C), the answer to step S41 becomes affirmative. Stated otherwise, the filter coefficient W(n) is of a value smaller than the second threshold value W2 {W(n)<W2} (corresponding to times t3, t7 in FIG. 7C).

Then, the microphone opening closure flag Fm is reset in step S43. At this time (time t3 or time t7 in FIG. 7C), it is not clear as to whether the microphone opening closed state is canceled or not. For immediately returning to the ordinary adaptive control process when the microphone opening closed state is canceled, the adaptive control process is performed from step S41 (YES) to step S43 to step S42 to step S1 to step S2 (YES) to step S3 as indicated in the period from time t3 to time t4 or from time t7 in FIG. 7C, thereby preventing the filter coefficient W(n) from becoming zero.

Specifically, when the microphone opening closure flag Fm is reset in step S43, the answer to step S2 becomes affirmative, and the adaptive control process in step S3 is performed. Since the answer to step S31 is affirmative, the count value cr is reset in step S32, and the filter coefficient W(n) set in the adaptive notch filter 14 is updated into the filter coefficient W(n+1)=W(n)+ΔW in step S33. The filter coefficient W(n) close to the second threshold value W2 as the lower limit value increases from time t3 or time t7 in FIG. 7B, increasing the control signal y(n).

During the period of the adaptive control process (here, the period from time t3 to time t4), i.e., in one of the period in which the process from step S1 to step S2 (YES) to step S31 (YES) to step S32 to step S33 to step S38 (NO) is repeated, the period in which the filter coefficient W(n) is set to the first threshold value W1 {W(n)=W1} and the control signal y(n) is kept as the preset upper limit value (from time t4 to time t5), and the period of the forgetting process (from time t5 to time t6), if the microphone opening closed state is canceled, then the ordinary adaptive control process is resumed from time t7. The adaptive control process is performed by the first filter coefficient updating means 51 to reduce noise in the passenger compartment.

According to the above embodiment, for preventing a continuous muffled sound from being generated when the opening 106 of the microphone unit 104 as a sound detector is closed, if the filter coefficient (first filter coefficient) W(n) of the adaptive notch filter 14 is of a value greater than the first threshold value W1, then the filter coefficient W(n) is set to the first threshold value W1 for a predetermined period for determining the microphone opening closed state, thereby limiting the control sound. When the predetermined period has elapsed, the forgetting process is performed to generate a canceling sound using the filter coefficient (calculated by the second filter coefficient updating means 52) W(n+1)=W(n)×λ which is produced by successively multiplying the filter coefficient to be updated (the first filter coefficient) W(n) by a predetermined value λ smaller than 1 (e.g., λ=127/128≈0.99). If the filter coefficient (calculated by the second filter coefficient updating means 52) W(n) is of a value smaller than the second threshold value W2 which is smaller than the first threshold value W1 while the canceling sound is being generated, then the adaptive control process is resumed, and the canceling sound is generated using the filter coefficient (calculated by the first filter coefficient updating means 51) W(n+1)=W(n)+ΔW that is successively updated to minimize the error sound.

As described above, the first threshold value (upper limit value) W1 and the second threshold value (lower limit value) W2 for the filter coefficient W(n) are provided, and when the filter coefficient W(n) becomes greater than the first threshold value W1, the control sound is faded out according to the forgetting process, and when the filter coefficient W(n) becomes smaller than the second threshold value W2, the adaptive control process is resumed. Therefore, even when the opening 106 of the microphone unit 104 is closed, the filter coefficient W(n) does not exceed the first threshold value W1 as the upper limit value, thereby preventing a continuous muffled sound from being generated and hence preventing the passengers from feeling uncomfortable with noise in the passenger compartment. Furthermore, because the noise cancellation process is continued with the filter coefficient W(n) being not zero, noise can immediately be lowered when the microphone opening closed state is canceled.

In the above embodiment, the switching means 54 performs its switching operation based on the value of the filter coefficient W(n). However, the switching means 54 may perform its switching operation based on the absolute values of the control signal y1(*n*) and the control signal y2(*n*).

Figure 8:
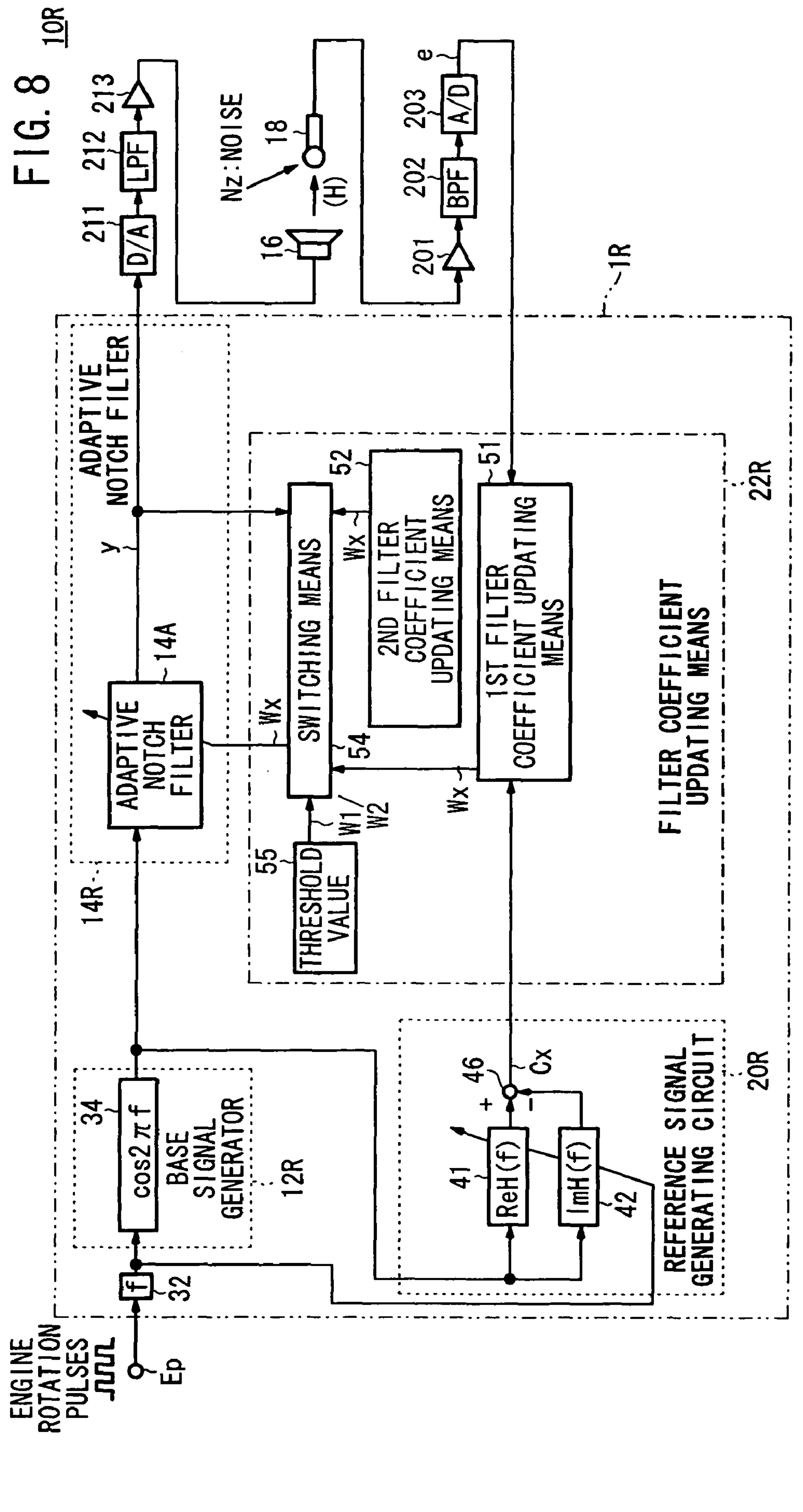
FIG. 8 is a block diagram of an active noise control system according to another embodiment of the present invention.

In the above embodiment, the base signal generator 12 generates a base wave signal representing a cosine wave cos {2π(f, n)} and a base wave signal representing a sine wave sin {2π(f, n)}. According to another embodiment shown in FIG. 8, an active noise control system 10R comprises a microcomputer 1R including a cosine wave generator 34 for generating only a base wave signal representing a cosine wave cos {2π(f, n)}. The active noise control system 10R is capable of reducing a continuous muffled sound and achieves some effects though its responsiveness and the amount of reduced noise are smaller than the active noise control system 10 shown in FIG. 1. The active noise control system 10R also includes a base signal generator 12R, a reference signal generating circuit 20R, an adaptive notch filter 14R, and a filter coefficient updating means 22R whose component costs are about half those of the active noise control system 10 shown in FIG. 1.

In the above embodiments, the active noise control systems 10, 10R are incorporated in the passenger compartment of the motor vehicle 30. However, the principles of the present invention are also applicable to any of various closed spaces, e.g., the passenger compartment of any of various other vehicles than the motor vehicle 30, cabins and rudder houses of ships, passenger cabins of amphibians, passenger cabins of pleasure boats, cabins of helicopters, cabins and cockpits of airplanes, etc.

Although certain preferred embodiments of the present invention have been shown and described in detail, it should be understood that various changes and modifications may be made therein without departing from the scope of the appended claims.

What is claimed is:

1. An active noise control system comprising:

a base signal generator for outputting a harmonic base signal from the frequency of noise generated by a noise source;

an adaptive notch filter for being supplied with said base signal and outputting a control signal for canceling out said noise;

a sound output unit for outputting a control sound represented by said control signal;

a sound detector for detecting a canceling error sound representing the difference between said noise and said control sound and outputting an error signal;

a correcting filter having a transfer function from said sound output unit to said sound detector, for being supplied with said base signal and outputting a reference signal;

first filter coefficient updating means for being supplied with said error signal and said reference signal and successively updating a filter coefficient of said adaptive notch filter in order to minimize said error signal;

second filter coefficient updating means for updating said filter coefficient by multiplying the filter coefficient to be updated of said adaptive notch filter by a predetermined value smaller than 1; and switching means for alternatively switching between said first filter coefficient updating means and said second filter coefficient updating means and supplying said filter coefficient to said adaptive notch filter;

wherein said switching means switches to a filter coefficient supplied from said second filter coefficient updating means when said filter coefficient is equal to or greater than a first threshold value and switches to a filter coefficient supplied from said first filter coefficient updating means when said filter coefficient is smaller than a second threshold value which is smaller than said first threshold value.

2. An active noise control system according to claim 1, wherein said base signal generator outputs a base sine wave signal and a base cosine wave signal as said harmonic base signal;

said adaptive notch filter comprising:

a first adaptive notch filter for outputting a first control signal based on said base cosine wave signal;

a second adaptive notch filter for outputting a second control signal based on said base sine wave signal; and an adder for adding said first control signal and said second control signal into said control signal and outputting the control signal to said sound output unit;

wherein said switching means switches to a filter coefficient supplied from said second filter coefficient updating means for said first adaptive notch filter and said second adaptive notch filter when either one of filter coefficients supplied respectively to said first adaptive notch filter and said second adaptive notch filter is equal to or greater than said first threshold value, and switches to a filter coefficient supplied from said first filter coefficient updating means for said first adaptive notch filter and said second adaptive notch filter when either one of the filter coefficients supplied respectively to said first adaptive notch filter and said second adaptive notch filter is smaller than said second threshold value.

3. An active noise control system according to claim 1, wherein said first threshold value and said second threshold value vary depending on the frequency of said base signal.

4. An active noise control system according to claim 2, wherein said first threshold value and said second threshold value vary depending on the frequency of said base signal.

5. An active noise control system according to claim 1, wherein said predetermined value is set to a value greater than 0.9.

6. An active noise control system according to claim 2, wherein said predetermined value is set to a value greater than 0.9.

* * * * *